United States Patent
Short

(10) Patent No.: US 8,783,453 B2
(45) Date of Patent: Jul. 22, 2014

(54) NEEDLE MAIL-BACK SYSTEMS AND METHODS OF MAKING AND USING THE SAME

(76) Inventor: Gregg R. Short, Solana Beach, CA (US)

(*) Notice: Subject to any disclaimer, the term of this patent is extended or adjusted under 35 U.S.C. 154(b) by 1029 days.

(21) Appl. No.: 12/205,096

(22) Filed: Sep. 5, 2008

(65) Prior Publication Data

US 2010/0058637 A1    Mar. 11, 2010

(51) Int. Cl.
*B65D 69/00*    (2006.01)
*B65D 71/00*    (2006.01)

(52) U.S. Cl.
USPC ............................ 206/232; 206/571; 206/365

(58) Field of Classification Search
USPC .................... 206/232, 340, 364, 365, 571
See application file for complete search history.

(56) References Cited

U.S. PATENT DOCUMENTS

| | | | | |
|---|---|---|---|---|
| 4,522,302 A * | 6/1985 | Paikoff | | 206/570 |
| 4,623,336 A * | 11/1986 | Pedicano et al. | | 604/192 |
| 4,917,867 A * | 4/1990 | Jensen et al. | | 422/102 |
| 5,024,326 A * | 6/1991 | Sandel et al. | | 206/366 |
| 5,038,929 A * | 8/1991 | Kubofcik | | 206/210 |
| 5,186,900 A * | 2/1993 | Jensen et al. | | 422/104 |
| 6,662,941 B2 * | 12/2003 | Lowry et al. | | 206/204 |
| 6,840,379 B2 * | 1/2005 | Franks-Farah et al. | | 206/571 |
| 2004/0031721 A1 * | 2/2004 | Mann | | 206/570 |
| 2004/0244202 A1 * | 12/2004 | Bull et al. | | 30/124 |
| 2007/0119739 A1 * | 5/2007 | Clegg et al. | | 206/365 |

* cited by examiner

*Primary Examiner* — Mickey Yu
*Assistant Examiner* — Rafael Ortiz
(74) *Attorney, Agent, or Firm* — Withers & Keys, LLC

(57) ABSTRACT

Needle mail-back systems and kits are disclosed. Methods of making and using needle mail-back kits are also disclosed. Methods of doing business involving needle mail-back systems and kits are also disclosed.

11 Claims, 2 Drawing Sheets

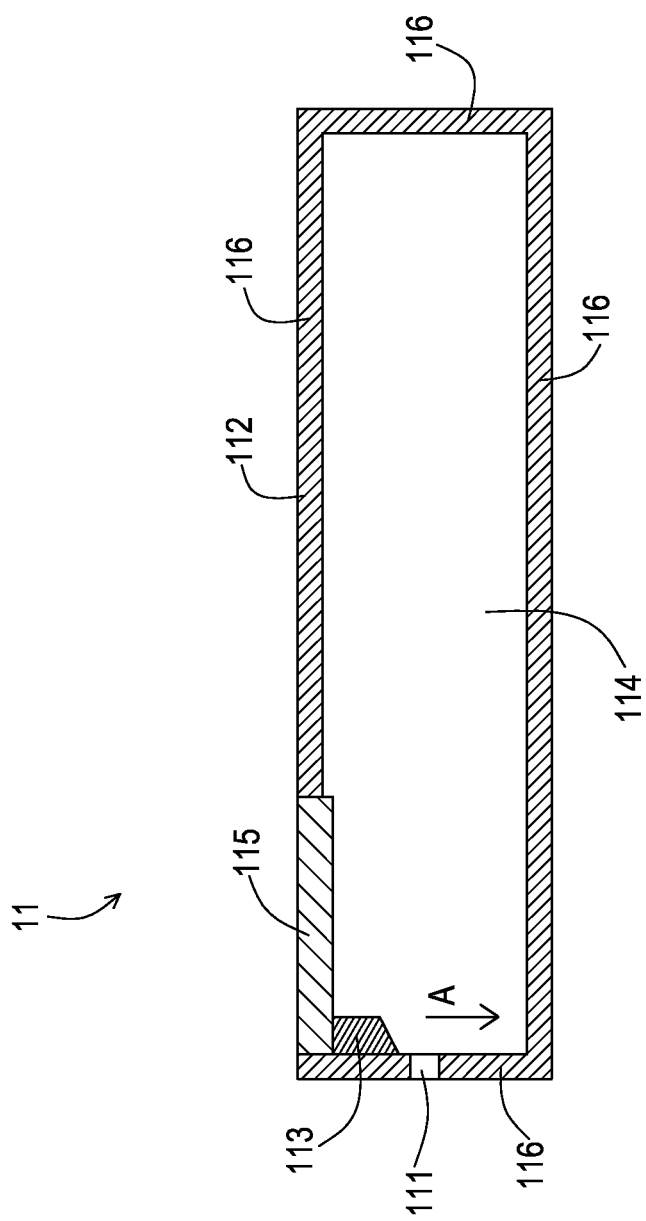

NEEDLE MAIL-BACK SYSTEMS AND METHODS OF MAKING AND USING THE SAME

FIELD OF THE INVENTION

The present invention relates generally to needle mail-back systems. The present invention further relates to methods of making and using needle mail-back systems. The present invention even further relates to methods of doing business involving needle mail-back systems.

BACKGROUND OF THE INVENTION

Mail-back systems for used syringes are known. However, known mail-back systems for used syringes have a number of shortcomings. For example, known mail-back systems do not attempt to separate the needle from the remaining portion of the syringe (i.e., the hollow barrel fitted with a plunger) so disposal of the syringe requires disposal of the needle as well as the hollow barrel and the plunger components of the syringe.

There is a need in the art for a mail-back system that efficiently disposes of used needles separate from other syringe components.

SUMMARY OF THE INVENTION

The present invention is directed to needle mail-back systems, which separate the needle portion of a syringe from a remaining portion of the syringe, namely, the hollow barrel and plunger of the syringe. The disclosed needle mail-back systems efficiently and safely enable proper disposal of waste needles, while minimizing efforts relating to the disposal of remaining syringe components (e.g., the hollow barrel, and the plunger). The disclosed needle mail-back systems provide a cost-effective and convenient method of properly disposing of used/waste needles without the additional costs associated with the disposal of other syringe components in known mail-back systems.

Accordingly, the present invention is directed to needle mail-back systems, and needle mail-back kits used therein. In one exemplary embodiment, the needle mail-back kit comprises an apparatus operatively adapted to separate a needle from a remaining portion of a syringe, the remaining portion of the syringe (i) being substantially free of a needle portion extending from the remaining portion of the syringe, and (ii) comprising a hollow barrel fitted with a plunger; a needle storage compartment; a sealable container comprising at least one layer of packaging material; and tracking documentation. The exemplary needle mail-back kit may further comprise one or more additional components such as a return envelope operatively adapted and sized for mailing the apparatus, the needle storage compartment (e.g., containing used needles), the sealable container, and the tracking documentation within a postal system; and a label on the return envelope, the label having a return address thereon.

The present invention is also directed to methods of making needle mail-back kits. In one exemplary embodiment, the method of making a needle mail-back kit comprises combining (1) an apparatus operatively adapted to separate a needle from a remaining portion of a syringe, the remaining portion of the syringe (i) being substantially free of a needle portion extending from the remaining portion of the syringe, and (ii) comprising a hollow barrel fitted with a plunger, (2) a needle storage compartment, (3) tracking documentation, (4) instructions for a customer explaining how to use the needle mail-back kit, (5) an optional sealable container comprising at least one layer of packaging material, and (6) a return envelope operatively adapted and sized for mailing the apparatus, the needle storage compartment, the tracking documentation and the optional sealable container within a postal system. The exemplary method of making a needle mail-back kit may further comprise providing a label for the return envelope, the label having a predetermined return address thereon.

The present invention is further directed to methods of using needle mail-back kits. In one exemplary embodiment, the method of using a needle mail-back kit comprises separating a needle of a syringe from a remaining portion of the syringe, the remaining portion of the syringe (i) being substantially free of a needle portion extending from the remaining portion of the syringe, and (ii) comprising a hollow barrel fitted with a plunger; collecting the needle in a needle storage compartment; and mailing the needle storage compartment to a predetermined address. The exemplary method of using a needle mail-back kit may further comprise one or more steps such as packaging the needle storage compartment (e.g., with used/waste needles therein) in a sealable container comprising at least one layer of packaging material; verifying whether personal information data or any other kit data is correct, and if the personal information data or any other kit data is incorrect, correcting the data; and including at least a portion of the tracking documentation within the sealable container.

The present invention is even further directed to methods of doing business involving needle mail-back kits. In one exemplary embodiment, the method of doing business comprises supplying a needle mail-back kit to a customer, the needle mail-back kit comprising an apparatus operatively adapted to separate a needle from a remaining portion of a syringe, the remaining portion of the syringe (i) being substantially free of a needle portion extending from the remaining portion of the syringe, and (ii) comprising a hollow barrel fitted with a plunger; a needle storage compartment; an optional sealable container comprising at least one layer of packaging material; tracking documentation; a return envelope operatively adapted and sized for mailing the apparatus, the needle storage compartment, the optional sealable container, and the tracking documentation within a postal system; and a label for the return envelope, the label having a return address thereon. The step of supplying a needle mail-back kit to a customer may comprise utilizing any entity to supply the needle mail-back kit to the customer. For example, a manufacturer (e.g., a kit or kit component manufacturer), a dealer or a retailer may be used to supply the needle mail-back kit to the customer.

In another exemplary embodiment, the method of doing business comprises receiving a needle mail-back kit from a customer, the needle mail-back kit comprising an apparatus operatively adapted to separate a needle from a remaining portion of a syringe, the remaining portion of the syringe (i) being substantially free of a needle portion extending from the remaining portion of the syringe, and (ii) comprising a hollow barrel fitted with a plunger; a needle storage compartment; a sealable container (and/or return envelope) comprising at least one layer of packaging material; tracking documentation; and one or more used needles within the needle storage compartment. The step of receiving a needle mail-back kit from a customer may comprise utilizing any entity to receive the needle mail-back kit from the customer. For example, a manufacturer (e.g., a kit or kit component manufacturer), a dealer, a retailer or a disposal facility may be used to receive the needle mail-back kit from the customer.

These and other features and advantages of the present invention will become apparent after a review of the following detailed description of the disclosed embodiments and the appended claims.

BRIEF DESCRIPTION OF THE FIGURES

The present invention is further described with reference to the appended figure, wherein:

FIG. 2 depicts a cross-sectional view of an exemplary needle clipping apparatus within the exemplary needle mail-back kit shown in FIG. 1 as viewed perpendicular to a plane containing line A-A shown in FIG. 1.

DETAILED DESCRIPTION OF THE INVENTION

Figure 1:
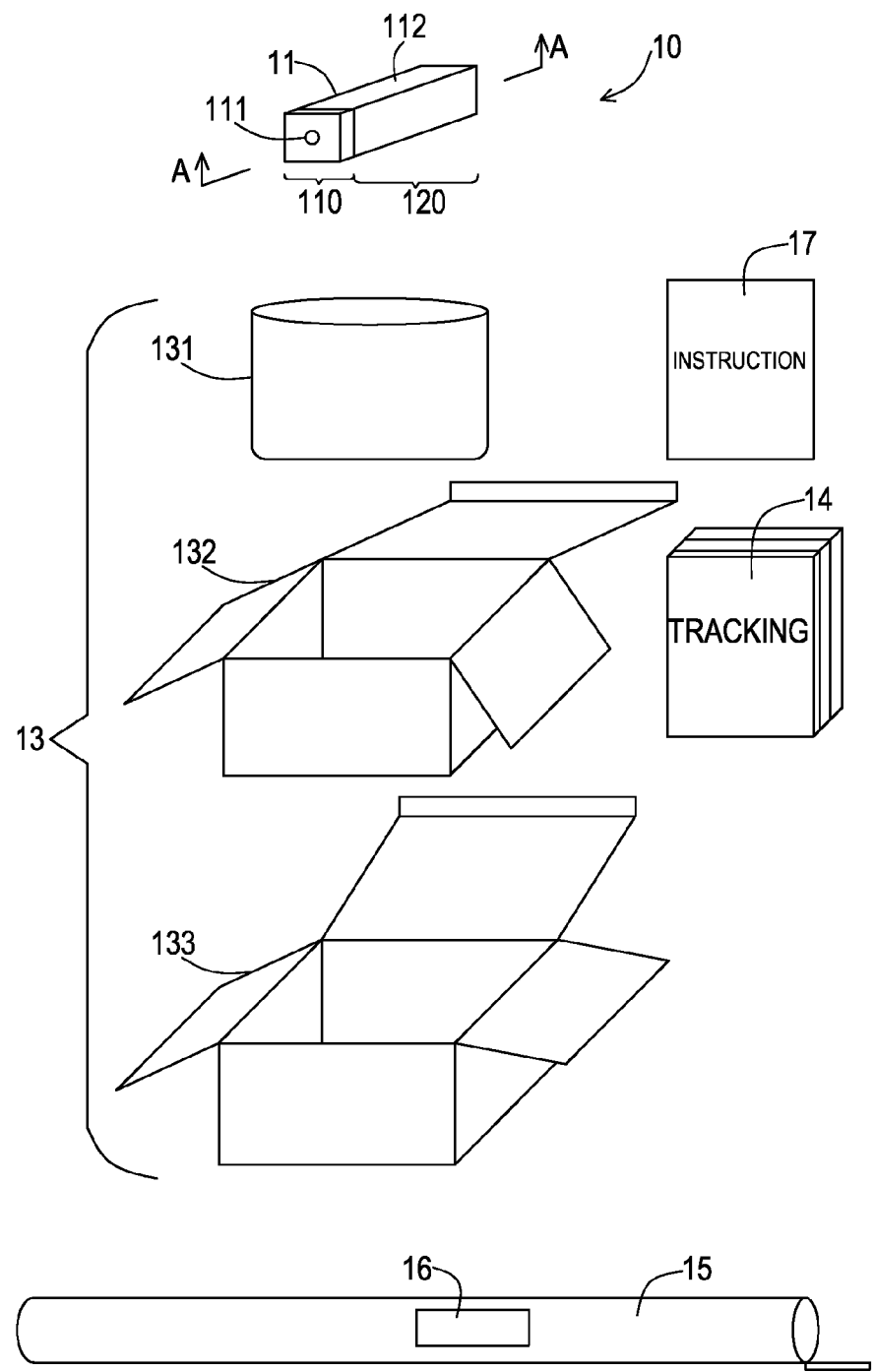
FIG. 1 depicts a perspective view of exemplary components within an exemplary needle mail-back kit of the present invention.

The present invention is directed to needle mail-back kits. The present invention is further directed to methods of making, as well as methods of using needle mail-back kits. The present invention is even further directed to methods of doing business involving needle mail-back kits.

The needle mail-back kits of the present invention may comprise a number of components. A description of individual components and combinations of individual components is provided below.

I. Needle Mail-Back Kit Components

The needle mail-back kits of the present invention may comprise one or more components either alone or in any combination with one another. Suitable components include, but are not limited to, (1) an apparatus operatively adapted to separate a needle from a remaining portion of a syringe, wherein the remaining portion of the syringe (i) is substantially free of a needle portion extending from the remaining portion of the syringe, and (ii) comprises a hollow barrel fitted with a plunger; (2) a needle storage compartment; (3) a sealable container comprising at least one layer of packaging material; (4) tracking documentation (i.e., documentation that enables the supplier of the kit, the user of the kit, the receiver of the used kit, and any other entity track the kit); (5) a return envelope operatively adapted and sized for mailing the apparatus, the needle storage compartment (e.g., containing used needles), the sealable container, and the tracking documentation within a postal system (e.g., the U.S. Postal Service); (6) a label for the return envelope, the label having a return address thereon; (7) instructions for the customer explaining how to use the needle mail-back kit (e.g., how to used the enclosed apparatus and how to return waste needles using the sealable container and return envelope); (8) a shipping container operatively adapted and sized for mailing the apparatus, the needle storage compartment, the sealable container, and the tracking documentation within the postal system (e.g., a shipping box, envelope, etc.); or any combination of items (1) to (8).

An exemplary needle mail-back kit of the present invention is shown in FIG. 1. As shown in FIG. 1, exemplary needle mail-back kit 10 comprises a needle separation apparatus 11, which comprises needle clipping mechanism 110 and a needle storage compartment 120, a sealable container 13, tracking documentation 14, a return envelope 15, a label 16 for placement on return envelope 15, label 16 having a return address thereon (label 16 is shown on return envelope 15, but could be provided separate therefrom), and instructions 17 for the customer (not shown) explaining how to use exemplary needle mail-back kit 10. Exemplary needle mail-back kit 10 may further comprise a shipping container (e.g., a shipping box slightly larger than outer box 133, an envelope sized to contain outer box 133, etc.) (not shown) operatively adapted and sized for mailing exemplary needle mail-back kit 10 to a customer within a postal system (e.g., the U.S. postal system).

In one desired embodiment, the apparatus operatively adapted to separate the needle from the remaining portion of a syringe comprises a needle clipping apparatus, and the needle storage compartment comprises a clipped needle storage compartment. In a further desired embodiment, the needle clipping apparatus and the clipped needle storage compartment are components of a single needle clipping apparatus such as exemplary needle separation apparatus 11. In this embodiment, the needle clipping apparatus separates the needle from the remaining portion of the syringe and automatically stores the clipped needle within the needle clipping apparatus.

As shown in FIG. 2, exemplary needle separation apparatus 11 comprises a housing 112 comprising housing wall 116, an opening 111 in housing wall 116 of housing 112 for insertion of a needle (not shown) therein, a needle clipping blade 113 within housing 112 and proximate opening 111, a blade-moving mechanism 115 that moves needle clipping blade 113 from a non-cutting position (i.e., the position as shown in FIG. 2) to a cutting position (i.e., to a position below opening 111 in a direction as shown by arrow A in FIG. 2), and needle storage compartment 114 within housing 112.

A number of needle clipping apparatus may be used in the needle mail-back kits of the present invention. Suitable needle clipping apparatus include, but are not limited to, needle clipping apparatus commercially available from The Insulin Case Shop (Chaska, Minn.) under the trade designations "Bd Safe Clip Needle Clipper" and "Clip & Stor Insulin Needle Clipper Safe Clip Safety System."

Each of the above-noted needle clipping apparatus clip the needle at the intersection of the needle with the hollow barrel portion of the syringe so that (i) there is a minimal length, if any, of needle remaining attached to and extending outward from the hollow barrel portion of the syringe, and (ii) the hollow barrel portion of the syringe is not damaged in any way.

The optional sealable container may comprise at least one layer of packaging material. In one embodiment, the sealable container is present and comprises an inner plastic bag sized so as to contain the needle separation apparatus and the needle storage compartment; an inner box sized so as to contain the needle separation apparatus and the needle storage compartment within the plastic bag; and an outer box sized so as to contain the inner box.

As shown in FIG. 1, exemplary needle mail-back kit 10 comprises sealable container 13, which comprises an inner plastic bag 131 sized so as to contain needle separation apparatus 11 (e.g., needle clipping mechanism 110 and needle storage compartment 120); an inner box 132 sized so as to contain needle separation apparatus 11 within plastic bag 131; and an outer box 133 sized so as to contain inner box 132. Plastic bag 131, inner box 132 and outer box 133 may each independently comprise one or more features that enable plastic bag 131, inner box 132 and/or outer box 133 to be sealed. Suitable features may include, but are not limited to, a zip-lock closure system for plastic bag 131, an adhesive seal for plastic bag 131, one or more box flaps on inner box 132 and/or outer box 133, and an adhesive seal for inner box 132 and/or outer box 133.

In other embodiments, the sealable container may act as the return shipping container. For example, in some embodiments, the sealable container comprises a padded envelope (e.g., similar to return envelope 15) that may be sealed. In this embodiment, the used/waste needles contained within a needle storage compartment (i.e., as part of a single needle separation apparatus or a separate component) are simply enclosed inside the padded envelope and shipped (e.g., mailed) within a postal service system. As with return envelope 15, a label such as label 16 having a return address thereon may be placed on the sealable container used as a shipping container/return envelope.

Once utilized, the needle separation apparatus results in used/waste needles. The used/waste needles may be stored in a needle storage compartment for a period of time sufficient to accumulate a plurality of needles within the needle storage compartment. As noted above, in some desired embodiments, the needle storage compartment is an integral component of the needle separation apparatus.

After use, the kit components are reassembled for shipping to a predetermined location for storage and/or disposal. The reassembled kit comprises the above-mentioned kit components (with or without the shipping container used to supply the kit to the customer), as well as used/waste needles within the needle storage compartment (e.g., clipped needles within the needle storage compartment). Desirably, the reassembled kit is substantially free of any syringe components other than the separated needles (e.g., the clipped needles).

II. Methods of Making Needle Mail-Back Kits

The present invention is further directed to methods of making the above-described needle mail-back kits. In one exemplary embodiment, the method of making a needle mail-back kit comprises combining any of the following components with one another: (1) an apparatus operatively adapted to separate a needle from a remaining portion of a syringe (e.g., the above-noted needle clipping apparatus), the remaining portion of the syringe (i) being substantially free of a needle portion extending from the remaining portion of the syringe, and (ii) comprising a hollow barrel (i.e., desirably, an undamaged hollow barrel) fitted with a plunger, (2) a needle storage compartment, (3) tracking documentation, (4) instructions for a customer explaining how to use the needle mail-back kit, (5) a sealable container comprising at least one layer of packaging material, and (6) a return envelope operatively adapted and sized for mailing the apparatus, the needle storage compartment, the tracking documentation and the sealable container within a postal system.

The methods of making a needle mail-back kit may further comprise one or more additional steps. Suitable additional steps include, but are not limited to, providing a label on the return envelope (or the sealable container), the label having a predetermined return address thereon; assigning an unique number (e.g., a Waste Manifest Tracking Number) for each kit; packaging the needle mail-back kit within a shipping container suitable for shipping (e.g., via mail) the needle mail-back kit within a postal service system (e.g., the U.S. postal service system); and personalizing a given needle mail-back kit for a specific customer.

III. Methods of Using Needle Mail-Back Kits

The present invention is even further directed to methods of using the above-described needle mail-back kits. In one exemplary embodiment of the present invention, the method of using a needle mail-back kit comprises separating a needle of a syringe from a remaining portion of the syringe, wherein the remaining portion of the syringe (i) is substantially free of a needle portion extending from the remaining portion of the syringe, and (ii) comprises a hollow barrel fitted with a plunger; collecting the separated needle in a needle storage compartment; and mailing the needle storage compartment containing one or more separated needles to a predetermined address.

The step of separating the needle portion of a syringe from the remaining portion of the syringe may comprise any step (or steps) necessary to separate the needle from the remaining portion of the syringe. Desirably, the separating step comprises clipping the needle from the remaining portion of the syringe via a needle clipping apparatus, such as the above-mentioned needle clipping apparatus, wherein the remaining portion of the syringe (i) is substantially free of a needle portion extending from the remaining portion of the syringe, and (ii) comprises a hollow barrel fitted with a plunger. In addition, desirably, the separating step does not damage the hollow barrel portion or the plunger portion of the syringe.

The separating and collecting steps may occur as a result of a single clipping step utilizing one of the above-mentioned needle clipping apparatus. In this embodiment, the needle clipping apparatus comprises a blade for clipping the needle, and a clipped needle storage compartment.

The methods of using a needle mail-back kit may further comprise one or more additional steps. Suitable additional steps include, but are not limited to, shipping (e.g., mailing) the assembled kit(s) to a given customer; discarding the remaining portion of the syringe in a trash receptacle (or other state mandated disposal receptacle), wherein the remaining portion of the syringe (i) is substantially free of a needle portion extending from the remaining portion of the syringe, and (ii) comprises a hollow barrel fitted with a plunger; packaging the needle storage compartment (i.e., containing one or more used/waste needles therein) in a sealable container comprising at least one layer of packaging material; reviewing personal information (e.g., customer name, customer mailing address, customer identification number, etc.) and tracking documentation of the needle mail-back kit; verifying whether personal information data or any other kit data is correct; if the personal information data or any other kit data is incorrect, correcting the data; including at least a portion of the tracking documentation within the sealable container and/or the return envelope; receiving a returned (e.g., used) kit from a given customer; documenting receipt of a returned (e.g., used) kit from a given customer; placing a returned (e.g., used) kit in a designated storage area; transporting one or more returned (e.g., used) kits from the designated storage area to a disposal facility; and treating the used/waste needles (e.g., autoclaving or any other proper medical waste treatment).

As discussed above, the methods of using a needle mail-back kit utilize a sealable container and/or a return envelope that provides one or more layers of material between the used/waste needles and anyone handling the reassembled kit. In some desired embodiments, the methods of using a needle mail-back kit utilize a sealable container comprising an inner plastic bag sized so as to contain the needle separation apparatus and the needle storage compartment containing one or more used/waste needles; an inner box sized so as to contain the needle separation apparatus and the needle storage compartment containing one or more used/waste needles within the plastic bag; and an outer box sized so as to contain the inner box. In other desired embodiments, the methods of using a needle mail-back kit utilize a sealable container that acts as the return envelope/shipping container.

IV. Methods of Doing Business Involving Needle Mail-Back Kits

The present invention is even further directed to methods of doing business involving the above-described needle mail-back kits. In one exemplary embodiment, the method of doing business comprises supplying a needle mail-back kit to a customer, the needle mail-back kit comprising an apparatus operatively adapted to separate a needle from a remaining portion of a syringe, the remaining portion of the syringe (i) being substantially free of a needle portion extending from the remaining portion of the syringe, and (ii) comprising a hollow barrel fitted with a plunger; a needle storage compartment; an optional sealable container comprising at least one layer of packaging material; tracking documentation; a return envelope operatively adapted and sized for mailing the apparatus, the needle storage compartment, the sealable container (when present), and the tracking documentation within a postal system; and a label for the return envelope (or sealable container), the label having a return address thereon. In some desired embodiment, the supplying step comprises mailing the needle mail-back kit to the customer.

In another exemplary embodiment, the method of doing business comprises receiving a needle mail-back kit from a customer, the needle mail-back kit comprising an apparatus operatively adapted to separate a needle from a remaining portion of a syringe, the remaining portion of the syringe (i) being substantially free of a needle portion extending from the remaining portion of the syringe, and (ii) comprising a hollow barrel fitted with a plunger; a needle storage compartment; a sealable container (or return envelope) comprising at least one layer of packaging material; tracking documentation; and one or more used/waste needles within the needle storage compartment.

The above exemplary methods of doing business may further comprise one or more additional steps. Suitable additional steps include, but are not limited to, collecting one or more used/waste needles in the needle storage compartment from the customer; instructing the customer to return the one or more used/waste needles within the needle storage compartment to a predetermined location; forwarding any received used/waste needles to a needle disposal facility; and properly disposing of the one or more used/waste needles (e.g., via an autoclaving step).

The present invention is described above and further illustrated below by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Preparation of a Clipped Needle Mail-Back Kit and Use Thereof

A clipped needle mail-back kit comprising the following components was prepared:
1. an instruction sheet;
2. a white shipping box kit with a biohazard symbol and return mailing label;
3. a brown inner box;
4. a plastic bag;
5. a needle clipping apparatus/clipped needle storage compartment;
6. a strip of tape; and
7. a serialized four-part tracking document in a plastic sleeve.

The above clipped needle mail-back kit was placed in an outer brown box and shipped to a customer at a first address.

The instruction sheet provided the following instructions to the customer:

Step 1—Save All Components!
1. Remove the white shipping box (e.g., the kit) from the delivery box (e.g., the outer brown box); discard the delivery box.
2. Open and retain the white shipping box.
3. Open the brown inner box, but DO NOT REMOVE from the white shipping box.
4. Open the plastic bag inside the brown inner box and remove the needle clipping apparatus/clipped needle storage compartment.
5. DO NOT discard outer white shipping box, brown inner box or the plastic bag. Save these packing items in a dry area. They must be used to reassemble the container system prior to mailing.

Step 2—Clip Needles into the Needle Clipping Apparatus/Clipped Needle Storage Compartment
1. Place the needle clipping apparatus/clipped needle storage compartment near point of use.
2. Squeeze grips indicated by arrows to open your needle clipping apparatus/clipped needle storage compartment.
3. With the compartment in the open position, fully insert needle. Then push down on thumb depression to clip needle. Compartment is now closed and needle is clipped
4. Keep compartment level. Discard remains of syringe or pen needle according to your local regulations. Clipped needle is automatically and safely retained within the needle clipping apparatus/clipped needle storage compartment. Holds up to 1,500 clipped needles.
5. Compartment can be used with needles including, but not limited to, 28 G through 31 G needles, ³⁄₁₆" (5 mm) through ½" (12.7 mm) length needles. Not intended for use with lancets Step 3—Seal the Container and Prepare System for Mailing
1. Place the needle clipping apparatus/clipped needle storage compartment into the plastic bag provided.
2. Then, insert the needle clipping apparatus/clipped needle storage compartment into brown inner box.
3. Close brown inner box by folding the small flaps down.
4. Close white shipping box containing the sealed inner box. Insert locking tab in the lid and seal shut with tape. ENSURE BOX IS SECURELY SEALED.

Step 4—Keep a Record
1. Remove four-part serialized Tracking Document from the plastic envelope affixed to the side of white shipping box. Complete Generator Information, sign and date Tracking Document. If your information is not printed or is not correct, print or correct the information prior to mailing the Home Sharps Disposal storage compartment.
2. Remove the back copy of the Tracking Document and retain for your records.
3. Place three remaining copies of Tracking Document into the plastic envelope affix to side of white box and close the envelope (insert any other required documents behind the Tracking Document). We maintain a record of your shipment.

Step 5—Mailing the Container System
1. Add return mailing address on Merchandise Return Service mailing label and attach to top of white outer shipping box. No P.O. Boxes allowed. Use of incorrect address is in violation of Postal Service regulations.

2. Give properly sealed container system to your postal route carrier, or drop off at any U. S. Post office for mailing.

Total Residual Fluid Allowed is Limited to 50 ml.

Total Weight Per System is Limited to 1 lb.

The customer followed the above instructions and the sealed container system was returned to a predetermined mailing address. The sealed container system was stored in a designated location. The sealed container system was subsequently transported from the storage area to an authorized waste disposal company, where the clipped needles within the needle clipping apparatus/clipped needle storage compartment were autoclaved (e.g., or treated using any other proper medical waste treatment) prior to disposal.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A needle mail-back kit comprising:
a needle clipping apparatus operatively adapted to clip a needle from a syringe;
a needle storage compartment;
a sealable container comprising at least one layer of packaging material;
tracking documentation; and
a label for return shipping, said label having a return address thereon;
wherein said needle storage compartment comprises a clipped needle storage compartment.

2. A needle mail-back kit comprising:
a needle clipping apparatus operatively adapted to clip a needle from a syringe;
a needle storage compartment;
a sealable container comprising at least one layer of packaging material;
tracking documentation; and
a label for return shipping, said label having a return address thereon;
wherein said sealable container comprises a return envelope that is operatively adapted and sized for mailing said needle clipping apparatus, said needle storage compartment, and said tracking documentation within a postal system.

3. A needle mail-back kit comprising:
a needle clipping apparatus operatively adapted to clip a needle from a syringe;
a needle storage compartment;
a sealable container comprising at least one layer of packaging material;
tracking documentation; and
a label for return shipping, said label having a return address thereon;
further comprising:
a return envelope operatively adapted and sized for mailing said needle clipping apparatus, said needle storage compartment, said sealable container, and said tracking documentation within a postal system; and sized for placement of said label having a return address thereon.

4. A needle mail-back kit comprising:
a needle clipping apparatus operatively adapted to clip a needle from a syringe;
a needle storage compartment;
a sealable container comprising at least one layer of packaging material;
tracking documentation; and
a label for return shipping, said label having a return address thereon;
wherein said sealable container comprises:
an inner plastic bag sized so as to contain said needle clipping apparatus and said needle storage compartment;
an inner box sized so as to contain said needle clipping apparatus and said needle storage compartment within said plastic bag; and
an outer box sized so as to contain said inner box.

5. A needle mail-back kit comprising:
a needle clipping apparatus operatively adapted to separate a needle from a syringe;
a clipped needle storage compartment;
a sealable container comprising:
an inner plastic bag sized so as to contain said needle clipping apparatus and said clipped needle storage compartment,
an inner box sized so as to contain said needle clipping apparatus and said clipped needle storage compartment within said plastic bag, and
an outer box sized so as to contain said inner box;
tracking documentation;
a label for return shipping of the clipped needle storage compartment, said label having a return address thereon;
a strip of tape; and
instructions explaining how to use said needle mail-back kit;
wherein said needle clipping apparatus comprises said needle storage compartment.

6. A needle mail-back kit comprising:
a needle clipping apparatus operatively adapted to separate a needle from a syringe;
a clipped needle storage compartment;
clipped needles within said clipped needle storage compartment;
a sealable container comprising at least one layer of packaging material;
tracking documentation; and
a label for return shipping, said label having a return address thereon;
wherein said sealable container comprises:
an inner plastic bag sized so as to contain said needle clipping apparatus and said clipped needle storage compartment;
an inner box sized so as to contain said needle clipping apparatus and said clipped needle storage compartment within said plastic bag; and
an outer box sized so as to contain said inner box.

7. A needle mail-back kit comprising:
a needle clipping apparatus operatively adapted to separate a needle from a syringe;
a clipped needle storage compartment;
clipped needles within said clipped needle storage compartment;
a sealable container comprising at least one layer of packaging material;
tracking documentation; and
a label for return shipping, said label having a return address thereon;

wherein said sealable container comprises:
- an inner plastic bag sized so as to contain said needle clipping apparatus and said clipped needle storage compartment;
- an inner box sized so as to contain said needle clipping apparatus and said clipped needle storage compartment within said plastic bag; and
- an outer box sized so as to contain said inner box;

further comprising:
- a return envelope operatively adapted and sized for mailing said needle clipping apparatus, said clipped needle storage compartment, said sealable container, and said tracking documentation within a postal system; and sized for placement of said label having a return address thereon.

8. A needle mail-back kit comprising:
a needle clipping apparatus operatively adapted to separate a needle from a syringe;
a clipped needle storage compartment;
clipped needles within said clipped needle storage compartment;
a sealable container comprising at least one layer of packaging material;
tracking documentation; and
a label for return shipping, said label having a return address thereon;
wherein said sealable container comprises:
- an inner plastic bag sized so as to contain said needle clipping apparatus and said clipped needle storage compartment;
- an inner box sized so as to contain said needle clipping apparatus and said clipped needle storage compartment within said plastic bag; and
- an outer box sized so as to contain said inner box;

further comprising:
- a return envelope operatively adapted and sized for mailing said needle clipping apparatus, said clipped needle storage compartment, said sealable container, and said tracking documentation within a postal system; and sized for placement of said label having a return address thereon;

wherein said kit is substantially free of any syringe components other than said clipped needles.

9. A needle mail-back kit comprising:
a needle clipping apparatus operatively adapted to clip a needle from a syringe;
a needle storage compartment;
a sealable container comprising at least one layer of packaging material;
tracking documentation; and
a label for return shipping, said label having a return address thereon;
further comprising:
- instructions explaining how to use said needle mail-back kit; and
- a strip of tape.

10. A needle mail-back kit comprising:
a needle clipping apparatus operatively adapted to separate a needle from a syringe;
a clipped needle storage compartment;
clipped needles within said clipped needle storage compartment;
a sealable container comprising at least one layer of packaging material;
tracking documentation; and
a label for return shipping, said label having a return address thereon;
wherein said sealable container comprises:
- an inner plastic bag sized so as to contain said needle clipping apparatus and said clipped needle storage compartment;
- an inner box sized so as to contain said needle clipping apparatus and said clipped needle storage compartment within said plastic bag; and
- an outer box sized so as to contain said inner box;

wherein said kit consists of said needle clipping apparatus; said clipped needle storage compartment; said clipped needles; said inner plastic bag; said inner box; said tracking documentation; said label; and a strip of tape.

11. A needle mail-back kit comprising:
a needle clipping apparatus operatively adapted to separate a needle from a syringe;
a clipped needle storage compartment;
clipped needles within said clipped needle storage compartment;
a sealable container comprising at least one layer of packaging material;
tracking documentation; and
a label for return shipping, said label having a return address thereon;
wherein said sealable container comprises:
- an inner plastic bag sized so as to contain said needle clipping apparatus and said clipped needle storage compartment;
- an inner box sized so as to contain said needle clipping apparatus and said clipped needle storage compartment within said plastic bag; and
- an outer box sized so as to contain said inner box;

wherein said kit consists of said needle clipping apparatus; said clipped needle storage compartment; said clipped needles; said inner plastic bag; said inner box; said tracking documentation; said label; and a strip of tape;
wherein said needle clipping apparatus and said needle storage compartment form a single apparatus that consists of a housing, an opening in said housing for insertion of a needle, a needle clipping blade within said housing and proximate said opening, a blade-moving mechanism that moves said needle clipping blade from a non-cutting position to a cutting position, and said needle storage compartment within said housing.

* * * * *